US008886311B2

(12) United States Patent
Anderson et al.

(10) Patent No.: US 8,886,311 B2
(45) Date of Patent: Nov. 11, 2014

(54) TECHNIQUES FOR MITIGATING MOTION ARTIFACTS FROM IMPLANTABLE PHYSIOLOGICAL SENSORS

(75) Inventors: David A. Anderson, Stanchfield, MN (US); Noah D. Barka, Coon Rapids, MN (US); Erin D. Grassl, Minneapolis, MN (US); Matthew D. Bonner, Plymouth, MN (US)

(73) Assignee: Medtronic, Inc., Minneapolis, MN (US)

( * ) Notice: Subject to any disclaimer, the term of this patent is extended or adjusted under 35 U.S.C. 154(b) by 75 days.

(21) Appl. No.: 13/360,149

(22) Filed: Jan. 27, 2012

(65) Prior Publication Data
US 2013/0197597 A1 Aug. 1, 2013

(51) Int. Cl.
A61N 1/365 (2006.01)

(52) U.S. Cl.
USPC .......................................... 607/18

(58) Field of Classification Search
USPC ............................... 607/17–26
See application file for complete search history.

(56) References Cited

U.S. PATENT DOCUMENTS

| 4,374,382 | A | | 2/1983 | Markowitz |
| 5,117,824 | A | | 6/1992 | Keimel et al. |
| 5,545,186 | A | | 8/1996 | Olson et al. |
| 5,554,177 | A | * | 9/1996 | Kieval et al. .................... 607/17 |
| 5,755,736 | A | | 5/1998 | Gillberg et al. |
| 6,393,316 | B1 | | 5/2002 | Gillberg et al. |
| 6,449,508 | B1 | | 9/2002 | Sheldon et al. |
| 6,643,548 | B1 | | 11/2003 | Mai et al. |
| 7,123,962 | B2 | | 10/2006 | Siejko et al. |
| 7,139,609 | B1 | | 11/2006 | Min et al. |
| 7,209,786 | B2 | | 4/2007 | Brockway et al. |
| 7,212,849 | B2 | | 5/2007 | Zhang et al. |
| 7,248,923 | B2 | | 7/2007 | Maile et al. |
| 7,343,915 | B2 | | 3/2008 | Addington et al. |
| 7,460,909 | B1 | | 12/2008 | Koh et al. |
| 7,689,283 | B1 | | 3/2010 | Schecter |
| 7,778,704 | B2 | * | 8/2010 | Rezai ................................ 607/9 |
| 7,787,946 | B2 | | 8/2010 | Stahmann et al. |
| 2004/0220636 | A1 | | 11/2004 | Burnes |
| 2005/0080461 | A1 | | 4/2005 | Stahmann et al. |
| 2007/0049977 | A1 | | 3/2007 | Von Arx et al. |
| 2007/0123943 | A1 | | 5/2007 | Patangay et al. |
| 2007/0142866 | A1 | | 6/2007 | Li et al. |
| 2007/0150014 | A1 | | 6/2007 | Kramer et al. |
| 2007/0150017 | A1 | | 6/2007 | Salo |
| 2008/0051839 | A1 | | 2/2008 | Libbus et al. |
| 2008/0082018 | A1 | | 4/2008 | Sackner et al. |
| 2008/0103399 | A1 | | 5/2008 | Patangay et al. |
| 2008/0195168 | A1 | | 8/2008 | Arand et al. |
| 2008/0215106 | A1 | * | 9/2008 | Lee et al. ......................... 607/17 |
| 2008/0234594 | A1 | | 9/2008 | Brooks et al. |
| 2008/0275349 | A1 | | 11/2008 | Halperin et al. |
| 2008/0294213 | A1 | | 11/2008 | Holmstrom et al. |

(Continued)

OTHER PUBLICATIONS

U.S. Appl. No. 13/474,041, by Zhang et al., filed May 17, 2012.

(Continued)

Primary Examiner — George Evanisko
(74) Attorney, Agent, or Firm — Michael C. Soldner

(57) ABSTRACT

Disclosed techniques include monitoring a physiological characteristic of a patient with a sensor that is mounted to an inner wall of a thoracic cavity of the patient, and sending a signal based on the monitored physiological characteristic from the sensor to a remote device.

23 Claims, 8 Drawing Sheets

(56) References Cited

U.S. PATENT DOCUMENTS

| | | | |
|---|---|---|---|
| 2009/0048640 | A1 | 2/2009 | Bauer et al. |
| 2009/0131999 | A1 | 5/2009 | Li et al. |
| 2009/0216138 | A1 | 8/2009 | Arand |
| 2009/0254139 | A1 | 10/2009 | Bjorling |
| 2010/0023078 | A1 | 1/2010 | Dong et al. |
| 2010/0069768 | A1 | 3/2010 | Min et al. |
| 2010/0073170 | A1 | 3/2010 | Siejko et al. |
| 2010/0087746 | A1 | 4/2010 | Radzievsky et al. |
| 2010/0185109 | A1 | 7/2010 | Zhang et al. |
| 2010/0198308 | A1 | 8/2010 | Zhou et al. |
| 2010/0312130 | A1 | 12/2010 | Zhang et al. |
| 2010/0331903 | A1 | 12/2010 | Zhang et al. |
| 2011/0015535 | A1 | 1/2011 | Lange et al. |
| 2011/0015703 | A1 | 1/2011 | Ternes et al. |
| 2011/0015704 | A1 | 1/2011 | Ternes et al. |
| 2011/0087079 | A1 | 4/2011 | Aarts |
| 2011/0196193 | A1* | 8/2011 | Forsell .......... 600/17 |
| 2011/0201871 | A1* | 8/2011 | Forsell .......... 600/16 |

OTHER PUBLICATIONS

U.S. Appl. No. 13/474,074, by Zhang et al., filed May 17, 2012.
Stec et al., "Premature ventricular complex-induced chronic cough and cough syncope," Eur Respir J. 2007:30 (2):391-394.
Toggweiler et al., "Visualizing Pacemaker-Induced Phrenic Nerve Stimulation with Acoustic Cardiography," PACE 2007;30:806-807.
Zuber et al., "Detection and Hemodynamic Significance of Cardiac Pacemaker-Induced Phrenic Nerve Stimulation," Congest Heart Fail. 2010:16:147-152.
Stahlberg et al., "Cardiac output response to changes of the atrioventricular delay in different body positions and during exercise in patients receiving cardiac resynchronization therapy," Europace (2009) 11: 1160-1167.
Zuber et al., "Systolic Dysfunction: Correlation of Acoustic Cardiography With Doppler Echocardiography," CHF. 2006; 12(4 supple 1): 14-18.
Auricchio et al., "Effect of Pacing Chamber and Atrioventricular Delay on Acute Systolic Function of Paced Patients With Congestive Heart Failure," Circulation 1999;99:2993-3001.
Baker, II et al., "Acute Evaluation of Programmer-Guided AV/PV and VV Delay Optimization Comparing an IEGM Method and Echocardiogram for Cardiac Resynchronization Therapy in Heart Failure Patients and Dual-Chamber ICD Implants," J Cardiovasc Electrophysiol, vol. 18, pp, 1-7, Jan. 2007.
Gold et al., "A Prospective Comparison of AV Delay Programming Methods for Hemodynamic Optimization during Cardiac Resynchronization Therapy," J Cardiovasc Electrophysiol, vol. 18, pp. 1-7. May 2007.
Gras et al., "Optimization of AV and VV Delays in the Real-World CRT Patient Population: An International Survey on Current Clinical Practice," PACE 2009;32:S236-23.
O'Donnell et al., "Long-Term Variations in Optimal Programming of Cardiac Resynchronization Therapy Devices," PACE 2005;28:S24-26.
Erne, "Beyond auscultation-acoustic cardiography in the diagnosis and assessment of cardiac disease," Swiss Med Wkly 2008;138(31-32):439-452.
U.S. Appl. No. 13/111,260, by Xusheng Zhang, filed May 24, 2011.
U.S. Appl. No. 13/111,260, by Xusheng Zhang, filed May 19, 2011.

* cited by examiner

TECHNIQUES FOR MITIGATING MOTION ARTIFACTS FROM IMPLANTABLE PHYSIOLOGICAL SENSORS

TECHNICAL FIELD

This disclosure relates to sensing physiological characteristics with implantable sensors.

BACKGROUND

Many sensor applications suffer from motion artifacts created by skeletal muscle motion during normal activities such as walking, hand/arm movement, and posture changes. A motion artifact often occurs in the same bandwidth as the signal of interest, and often has amplitudes large enough to saturate the amplifiers used for signal acquisition. A great deal of effort has been focused on elimination of motion artifact using signal-processing techniques.

SUMMARY

In general, the disclosure is directed to techniques for minimizing motion artifacts in sensor data of implantable sensors. The disclosed techniques include sensing at a location that mitigates skeletal muscle interaction with the sensing element of an implantable sensor. The techniques may include monitoring physiological characteristics of a patent with one or more implantable sensors located within a patient's thoracic cavity. Positions within a patient's thoracic cavity may substantially mitigate motion artifacts from the sensor signal(s).

In one example, this disclosure is directed to a method comprising: monitoring a physiological characteristic of a patient with a sensor that is mounted to an inner wall of a thoracic cavity of the patient, and sending a signal based on the monitored physiological characteristic from the sensor to a remote device.

In another example, this disclosure is directed to a method comprising monitoring sounds with a sound sensor that is mounted to an inner wall of a thoracic cavity of a patient, and sending a sound signal based on the monitored sounds from the sound sensor to a controller of an implantable medical device implanted within the patient.

In another example, this disclosure is directed to a method for implanting a sound sensor comprising accessing a thoracic cavity of a patient, controlling air pressure within a thoracic cavity of the patient via a vacuum to mitigate a risk of lung collapse during implantation of the sound sensor, positioning the sound sensor within the thoracic cavity of the patient, and securing the sound sensor to an inner wall of the thoracic cavity.

In another example, this disclosure is directed to system comprising an implantable medical device, and a sound sensor configured to mount to an inner wall of a thoracic cavity of a patient, wherein the sound sensor is further configured to send a sound signal based on sounds monitored from within the thoracic cavity to the implantable medical device. The implantable medical device is configured to receive the sound signal from the sound sensor and generate a physiological metric based on the received sound signal.

The details of one or more examples of this disclosure are set forth in the accompanying drawings and the description below. Other features, objects, and advantages of this disclosure will be apparent from the description and drawings, and from the claims.

DETAILED DESCRIPTION

Figure 1:
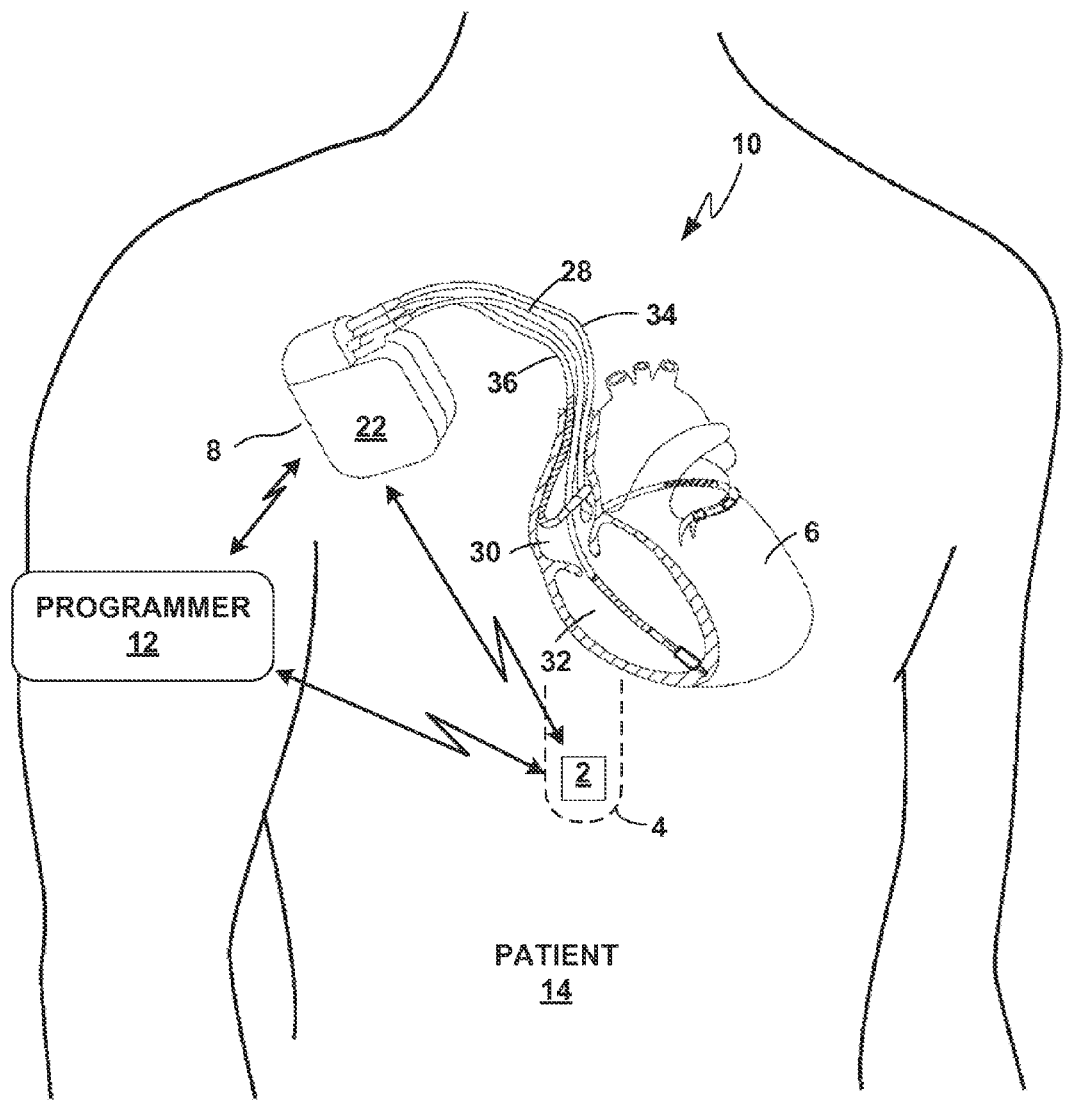
FIG. 1 is a conceptual diagram illustrating an example system that includes a sensor, a programmer and an implantable medical device (IMD) coupled to a plurality of leads that may be used to monitor one or more physiological parameters of a patient and/or provide therapy to the heart of a patient.

In general, this disclosure is directed to techniques for sensing physiological characteristics with implantable sensors in a manner that mitigates motion artifacts. The disclosed techniques include sensing at a location that mitigates skeletal muscle interaction with the sensing element of an implantable sensor, such as a location on an interior wall of the thoracic cavity of a patient. One such location is beneath the xyphoid process. While there are muscles terminating at the sternum, there is limited tissue directly beneath the xyphoid process and sternum. For this reason, a sensor element located beneath the sternum is not corrupted by muscle movement causing pressure changes on the sensing element or tissue changes as the muscle slides over the sensing element. Described techniques may substantially mitigate motion artifacts from sensor signals observed when monitoring the heart.

In one example, heart sounds are obtained from an implanted heart sound sensor that is secured to an interior wall of the thoracic cavity of a patient. Positioning the heart sound sensor within the thoracic cavity of the patient substantially mitigates motion artifacts that can be caused by muscle tissue and, thereby limits the need for filtering the sound signal when using the sound signal to generate a cardiac metric.

Heart sounds may be used to generate cardiac metrics. However, sound signals from sensors that detect heart sounds generally include a variety of other components in addition to the heart sounds. For example, a sound signal may include breathing artifacts and skeletal muscle motion artifacts. As examples, skeletal muscle motion artifacts may be created by skeletal muscle motion during normal activities such as walking, hand or arm movement, and posture changes. Because sound signals generally include a variety of components in addition to heart sounds, generating a cardiac metric based on detected sounds generally requires filtering the undesired components of the sound signal, such as, e.g., breathing artifacts and skeletal muscle motion artifacts, from the sound signal.

In one specific example, a sound sensor may be secured to the sternum within thoracic cavity of a patient. While there are muscles terminating at the sternum, there is limited tissue directly beneath the xiphoid process and sternum within the thoracic cavity. Sounds detected by such a sound sensor would not be corrupted by, for example, muscle movement causing pressure changes on the sensing element or tissue changes as the muscle slides over the sensing element. There are few skeletal muscles to interfere with a sound sensor positioned on an inner wall of a thoracic cavity of a patient. Locations for implantation on an inner wall of a thoracic cavity of a patient may include, for example, the sternum, ribs, or sub-xiphoid process. The resulting signal, which may be substantially free from motion artifacts, can then be used to generate, based at least in part on the heart sounds and the EGM, one or more cardiac metrics.

Heart sounds are associated with mechanical vibrations of a patient's heart and the flow of blood through the heart, and thus, are highly correlated with pressure gradients across heart valves and blood pressure, and when listened to by a clinician, may reveal abnormalities in cardiac structure or function. Heart sounds are created by not only vibrations of and pressure within the heart, but may be due to the whole cardiohemic system, e.g., blood, heart, great arteries, etc. Heart sounds recur with each cardiac cycle and are separated and classified according to the activity associated with the vibration.

The first commonly observed heart sound is referred to as "S1" and can be thought of as the vibrational sound made by the heart during closure of the atrioventricular (AV) valves, i.e., the mitral valve and tricuspid valve. The S1 sound can sometimes be broken down into an M1 component, associated with the closure of the mitral valve, and a T1 component, associated with the closing of the tricuspid valve. The second heart sound is referred to as "S2," and results from the closure of the semilunar valves, i.e., the pulmonary and aortic valves. The S2 heart sound can be thought of as marking the beginning of diastole. The S2 sound can also be broken down into component parts. The P2 component is associated with the closing of the pulmonary valve and A2 component is associated with the closing of the aortic valve. The third and fourth heart sounds are referred to as "S3" and "S4," respectively, and can be conceptualized as related to filling of the ventricles during diastole. S3 is due to rapid filling of the ventricles and can occur when the ventricular wall is not relaxed when a large volume of blood flows into the ventricle from the atria. S4 is caused by blood rapidly filling into the ventricles from the atria due to atrial contraction.

As used herein, the term heart sound refers to any feature of a heart sound signal, such as the S1, S2, S3, or S4 heart sounds described above or other heart sounds or sounds created elsewhere in the cardiohemic system. There may be multiple heart sounds, e.g., each of an S1, S2, S3 and S4 heart sound, for any given cardiac cycle or heartbeat.

To monitor the heart sounds, a heart sound sensor, such as a piezoelectric sensor or other acoustic sensor, may implemented with an implantable medical device (IMD), e.g., on a lead or within a housing of the IMD. Alternatively, a heart sound sensor may be implanted separately and include a telemetry module allowing for wireless communication between the heart sound sensor and the IMD. Contained in separate housing, the heart sound sensor can be implanted in areas more advantageous for target location sensing.

Heart sounds may provide important information about the mechanical function of a heart. For instance, a cardiac metric may represent a characterization of cardiac function, such as an increase in the amplitude of the S3 sound, which may be associated with elevated left ventricle (LV) filling pressure, which may, in turn, be associated with worsening heart failure. The S4 sound is caused by atrial contraction, and becomes pronounced when the left ventricle loses its compliance due to, for example, acute myocardial infarction and ischemia. The amplitude of S1 heart sound has been shown to correlate with the maximum rate of rise of left ventricular pressure (LV dP/dt Max), which is a measure of cardiac contractility. The interval between Q-wave (or R-wave) from the EGM and the S1 heart sound represents both the delay between electrical activation and mechanical contraction of the ventricle. This is often referred to as the electromechanical activation time (EMAT). The shortening of the interval has been predictive of response to CRT. An interval from S1 to S2 sounds represents ejection time (ET) which is correlated with stroke volume and cardiac output. Any characterization of the mechanical or electrical function of a heart, including those mentioned herein, maybe used in the generation of a cardiac metric based on heart sounds.

Heart sounds can approximately provide similar mechanical function assessment for the heart as echocardiography (Echo), without the need for a patient to travel to a doctor's office, and without the need for Echo equipment. For example, Echo may provide left-ventricular diastolic filling time, collided E and A waves, and mitral valve incompetence with late diastolic regurgitation, which may be used to assess AV dyssynchrony. Correspondingly, heart sounds can provide the interval from S2 to S1 sound, the interval from S2 to S4 sounds, and the interval from S4 to S1 sounds, as well as the S1 acceleration time, for assessment AV dyssynchrony. Echo may provide a difference between aortic and pulmonary pre-ejection times (i.e., the interval from the start of pulmonary flow to the beginning of aortic flow), which may be used to assess interventricular (VV) dyssynchrony.

For assessment of left intraventricular dyssynchrony, Echo may provide the aortic pre-ejection interval, time to isovolumic contraction and septal-to-posterior wall motion delay. Heart sounds can be used to determine the EMAT plus S1 duration, EMAT, and M1 duration or A2 duration, which may indicate the degree of left intraventricular dyssynchrony. A myocardial performance index (MPI) determined from Echo may be used to assess both systolic and diastolic function. The ratio of (S1 duration+S2 duration)/(interval between S1 and S2) determined based on heart sounds may be used as an approximate surrogate for MPI.

To monitor the heart sounds, a heart sound sensor, such as a piezoelectric sensor or other acoustic sensor, may implemented with an IMD that delivery a cardiac therapy, e.g., on a lead or within a housing of the IMD that delivery a cardiac therapy. Alternatively, a heart sound sensor may be implanted separately and include a telemetry module allowing for wireless communication between the heart sound sensor and a remote device, such as a programmer or an IMD that delivers a cardiac therapy. Contained in separate housing than an IMD that delivers a cardiac therapy, the heart sound sensor can be implanted in areas more advantageous for target location sensing. The heart sound sensor can be implanted in areas away from skeletal muscle, so that the motion artifacts from skeletal muscles are substantially mitigated in the sound signal picked up by the sensor.

As seen above, heart sounds based cardiac metrics are available as approximations for Echo-based cardiac metrics. Unlike Echo-based cardiac metrics, the heart sounds based cardiac metrics may be done automatically inside an IMD itself. In this manner, a patient does not need to visit a physician for additional reading by a remote device, because the IMD may process heart sounds and/or EGM signals. In other examples, remote device may be used to generate a cardiac metric based on heart sounds and/or EGM signals.

In different examples, a cardiac metric may be a generated measurement of the performance of the patient's heart, and can be based on many different factors. In this manner, a cardiac metric may represent a characterization of any aspect of the performance or function of the patient's heart. A cardiac metric can be, for example, based on any one of, or combination of, heart sounds or electrical sensing of the cardiac signal. In some examples, a generated cardiac metric may be based on a heart sound, pressure within the heart, and/or a cardiac EGM.

FIG. 1 is a conceptual diagram illustrating an example system 10. System 10 includes sensor 2. In one example, sensor 2 is a sound sensor configured to detect heart sounds from within a thoracic cavity of patient 14. Sensor 2 is located beneath the xyphoid process and on an interior wall of the thoracic cavity. System 10 further includes IMD 8 and programmer 12. IMD 8 is configured to receive heart sound information from sensor 2. Programmer 12 is configured to communicate wirelessly with sensor 2 and/or IMD 8. One or more of sensor 2, IMD 8 and programmer 12 is configured to generate a cardiac metric based at least in part on sounds monitored by sensor 2, the cardiac metric representing some aspect of the function of heart 6.

Any recordation, categorization or assessment of a sound signal that includes a heart sound represents generation of a cardiac metric based on the heart sound. Heart sound and EGM signals contain specific information regarding electrical, mechanical, contractility and left ventricle filling functions of the patient's heart. Accordingly, combinations of heart sounds and EGM signals may also be used to generate cardiac metrics. In system 10, for example, EGM signals sensed by IMD 8 may be combined with heart sounds monitored by sensor 2 to generate a cardiac metric.

System 10 includes IMD 8, which is connected to leads 28, 34, and 36. IMD 8 may be configured to sense electrical signals attendant to the depolarization and repolarization of heart 6, e.g., a cardiac EGM, via electrodes on one or more leads 28, 34 and 36 or the housing of IMD 8. IMD 8 may also deliver therapy in the form of electrical signals to heart via electrodes located on one or more leads 28, 34 and 36 or a housing of IMD 8. In different examples, the therapy may include pacing, cardioversion and/or defibrillation pulses. IMD 8 also includes a telemetry module that facilitates wireless communications with sensor 2. In other examples, IMD 8 may communicate with sensor 2 via a wired connection. IMD 8 may similarly include or be couple to other sensors, such as one or more accelerometers, for detecting other physiological parameters of patient 14, such as activity or posture.

System 10 further includes sensor 2. Separating sensor 2 from IMD 8 allows sensor 2 to be positioned within the thoracic cavity of patient 14, such as within the thoracic cavity of patient 14 and secured to an inner wall of the thoracic cavity. In system 10, sensor 2 is located on sternum 4 and within the thoracic cavity of patient 14. In other examples, sensor 2 can be located within IMD 8 or a separate device that can be secured to an inner wall of the thoracic cavity on bone, cartilage or other patient tissue in the thoracic cavity of patient 14. Locating sensor 2 on a bone or cartilage, such as the sternum, ribs, or xiphoid process, within the thoracic cavity of patient 14 mitigates motion artifacts from skeletal muscle motion during the detection of heart sounds. For example, motion artifacts may occur in the same bandwidth as the heart sound signal. Motion artifacts may also have amplitudes large enough to saturate the amplifiers used for signal acquisition, rendering the output signal difficult to read or unusable. In such cases, signal-processing techniques may not be available to remove the motion artifacts, and the motion artifacts may substantially corrupt the heart sound signal. In addition, less extensive signal processing may be necessary when a signal includes fewer or less pronounced artifacts, which may reduce battery consumption and improve device longevity.

A signal representing detected heart sounds may be sent to IMD 8 and/or programmer 12 from sensor 2 via wired or wireless communication using any techniques known in the art, for example low frequency or radiofrequency (RF) telemetry, Bluetooth® and other techniques. In some examples, sensor 2 and/or IMD 8 could communicate with another wireless monitoring device other than programmer 12 such as a cellular phone or other consumer electronic device.

While sensor 2 is described in one example as being a sound sensor, in other examples, sensor 2 may include additional sensing elements such as one or more optical sensing elements and/or one or more electrical sensing elements. As one example, optical sensing elements may be used to monitor perfusion and/or oxygenation within an adjacent vasculature. Such electrical sensing elements may be used to sense impedance, e.g., of lung tissue, and/or electrical potential, such as with an ECG. In further examples, sensor 2 may not include a sound sensor, but may include one or more electrical sensing elements and/or optical sensing elements.

As one example, sensor 2 may include one or more optical sensing elements to, e.g., optically monitor blood flow or blood oxygenation through vasculature adjacent sensor 2. Locating sensor 2 on a bone or cartilage, such as the sternum, ribs, or xiphoid process, within the thoracic cavity of patient 14 mitigates motion artifacts from skeletal muscle motion during the monitoring of blood flow or blood oxygenation.

As another example, sensor 2 may include one or more electrical sensors. In some examples electrical sensors may be used to monitor impedance, e.g., for lung wetness and/or cardiac applications (filling waveforms etc.) and may also be used to monitor electrical potential, such as with ECG signals. In other examples, sensor 2 may not include a sound sensor, but may include one or more electrical sensing elements, one or more optical sensing elements or any combination thereof. Locating sensor 2 on a bone or cartilage, such as the sternum, ribs, or xiphoid process, within the thoracic cavity of patient 14 mitigates motion artifacts from skeletal muscle motion during the electrical sensing. For example, with electrical sensing using an IMD mounted proximate to a patient's pectoral muscles, the relative movement of the IMD and associated leads or other sensing elements may create motion artifacts within the signal of the electric sensors.

Motion artifacts may occur in the same bandwidth as heart sound signals, optical signals and electrical signals. Motion artifacts may also have amplitudes large enough to saturate the amplifiers used for signal acquisition, rendering the output signal difficult to read or unusable. In such cases, signal-processing techniques may not be available to remove the motion artifacts, and the motion artifacts may substantially corrupt heart sound signals, optical signals and electrical signals. In addition, less extensive signal processing may be necessary when a signal includes fewer or less pronounced artifacts, which may reduce battery consumption and improve device longevity.

Many securing techniques compatible with bone or cartilage can be utilized to anchor sensor 2 to an inner wall of the thoracic cavity, such as sutures, pins, spring-loaded anchors, self-actuating anchors released during implantation, such as nitinol anchors, adhesive, cement, bone morphogenic protein, using a suction device, or any combination thereof.

In some examples, programmer 12 takes the form of a handheld computing device, computer workstation or networked computing device that includes a user interface for presenting information to and receiving input from a user. A user, such as a physician, technician, clinician, electro-physiologist, or other clinician, may interact with programmer 12 to retrieve physiological or diagnostic information from IMD 8. A user may also interact with programmer 12 to program IMD 8, e.g., select values for operational parameters of IMD 8 and/or sensor 2. In certain examples, various functions of the programmer 12 may be automated. For example, the operational parameters may be selected automatically in response to one or more cardiac metrics, such as cardiac metrics based at least in part on heart sounds monitored by sensor 2.

In other examples, some or all of the functions ascribed to IMD 8 or a processor thereof may be performed by one or more other devices, such as programmer 12, or a processor thereof. For example, programmer 12 may process heart sound and/or cardiac EGM signals received from IMD 8 to determine whether a therapy should continue to be delivered based on current pacing parameters and control under what pacing parameters IMD 8 delivers the therapy. Furthermore, although described herein with respect to an IMD 8, in other examples, the techniques described herein may be performed or implemented in an external medical device, which may be coupled to a patient via percutaneous or transcutaneous leads.

Figure 2:
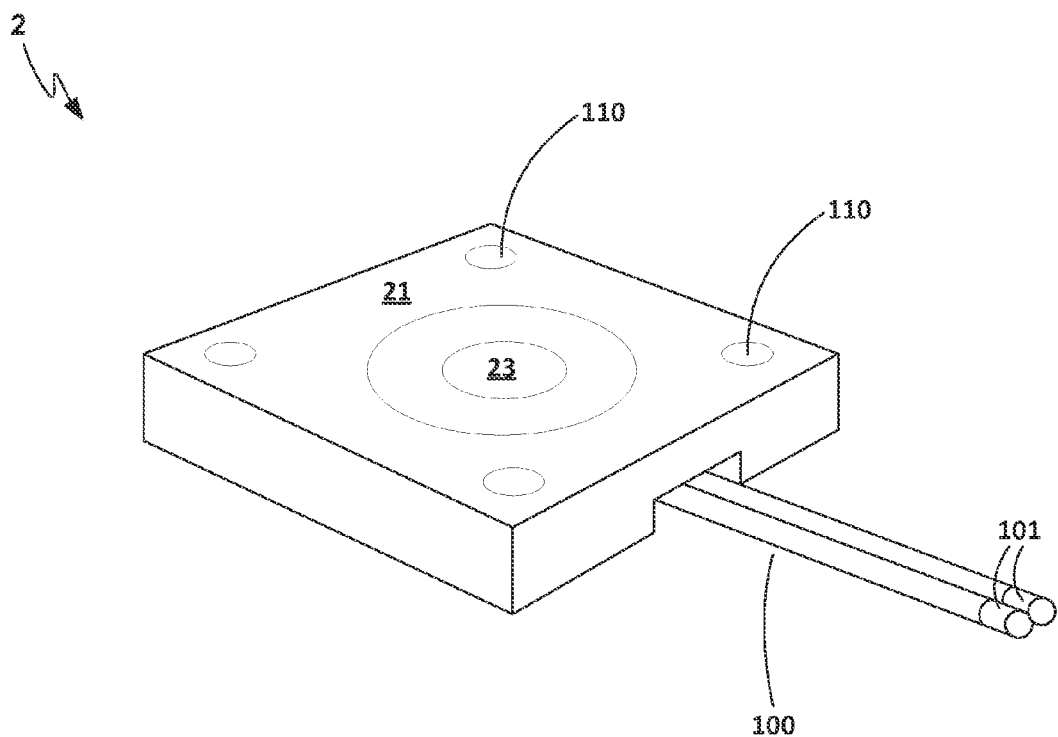
FIG. 2 is a schematic illustrating a heart sound sensor.

FIG. 2 is a schematic of sound sensor 2. As an example, sound sensor 2 shown in FIG. 2 may be substantially similar to sensor 2 as illustrated in system 10 of FIG. 1. Sounds sensor 2 is configured to be small enough to facilitate minimally invasive surgical implantation.

Sound sensor 2 includes a housing 21 containing a sound sensing element 23. Housing 21 forms holes 110, which facilitate securing sound sensor 2 to a patient tissue with sutures? In other examples, a sound sensor similar to sounds sensor 2 may be anchored to a target location within a using other techniques. Many securing techniques are compatible with bone or cartilage, and can be utilized to anchor a sound sensor to an inner wall of the thoracic cavity, such as sutures, pins, spring-loaded anchors, self-actuating anchors released during implantation, adhesive, cement, bone morphagenic protein, or using a suction device.

As shown in FIG. 2, sounds sensor 2 further includes leads 100, which include sensing electrodes 101. In some examples, sensing electrodes 101 may be configured to monitor cardiac signals. In other examples, sensing electrodes 101 may be used to measure impedance of a patient tissue, such as the impedance of lung tissue of the patient 14. In other examples, a sound sensor may include sensing electrodes for monitoring cardiac signals and for measuring impedance of a patient tissue.

Within housing 21, sound sensor 2 further includes a power source, such as a battery or inductive coil, control electronics, and a communication module to facilitate communication with a remote device, such as IMD 8 or programmer 12, as described with respect to FIG. 1.

Figure 3:
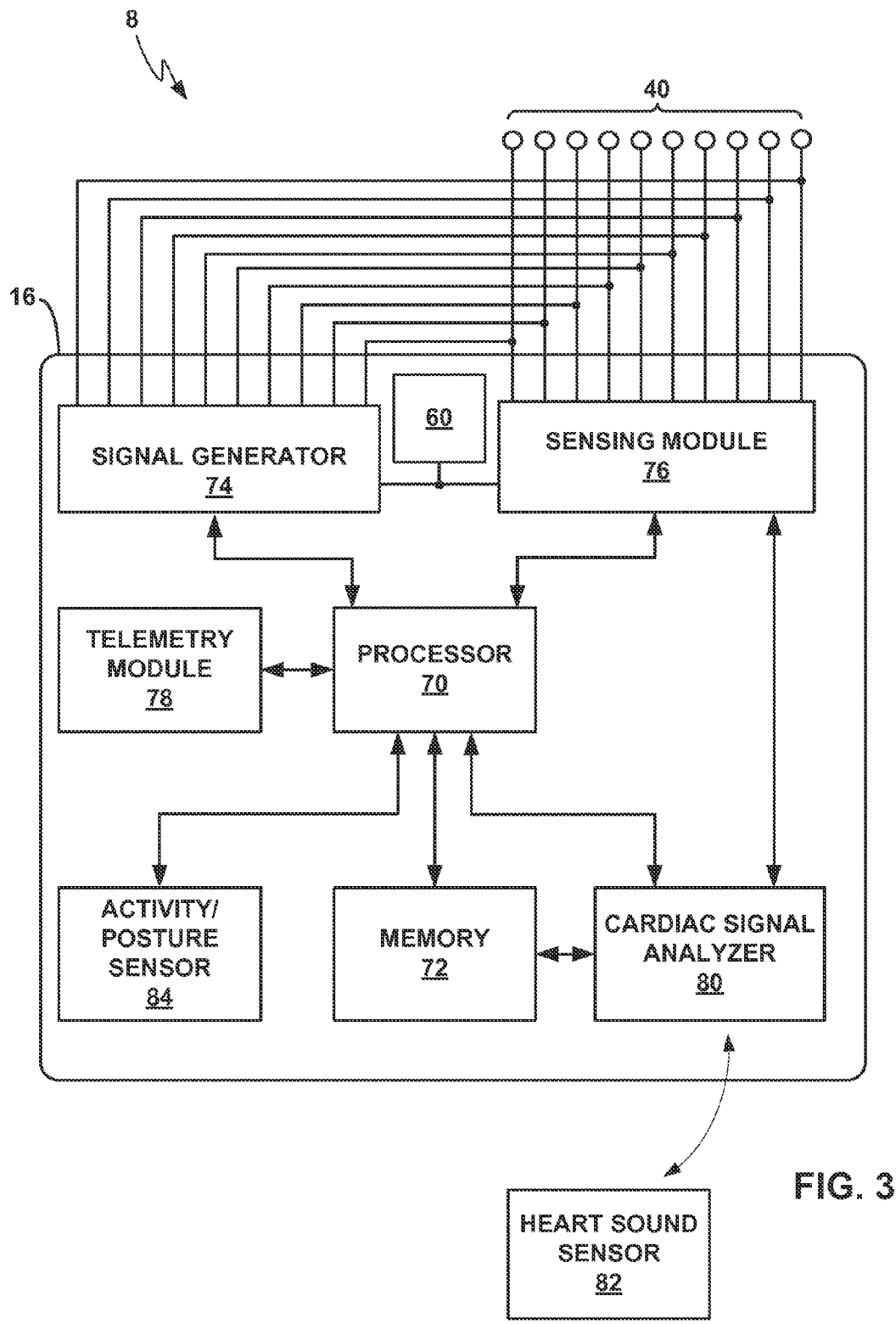
FIG. 3 is a block diagram illustrating an example configuration of the IMD of FIG. 1.

FIG. 3 is a block diagram illustrating an example configuration of components within housing 16 of IMD 8. Housing 16 may enclose a signal generator 74 that generates therapeutic stimulation, such as cardiac pacing, cardioversion, and defibrillation pulses, as well as a sensing module 76 for sensing electrical signals attendant to the depolarization and repolarization of heart 6 (FIG. 1). IMD 8 may also include or communicate with a heart sound sensor 82 that generates an electrical signal based on sensed heart sounds. In some examples, the heart sound sensor 82 may be enclosed within housing 16.

Signal generator 74 is configured to generate and deliver electrical stimulation therapy to patient 12. As shown in FIG. 3, signal generator 74 is electrically coupled to electrodes 40, e.g., via conductors of the respective leads 28, 34, and 36 and, in the case of housing electrode 60, within housing 16.

IMD 8 senses electrical signals attendant to the depolarization and repolarization of heart 6 via electrodes 40. IMD 8 may sense such electrical signals via any bipolar combination of electrodes 40. Furthermore, any of the electrodes 40 may be used for unipolar sensing in combination with housing electrode 60.

In some examples, IMD 8 delivers pacing pulses via bipolar combinations chosen based on heart sounds and/or EGM signals as analyzed by cardiac signal analyzer 80. For example, bipolar combinations of electrodes 40 may be used to produce depolarization of cardiac tissue of heart 6. In some examples, IMD 8 delivers pacing pulses via any of electrodes 40 in combination with housing electrode 60 in a unipolar configuration. The particular electrodes delivering pulses may be determined based in part on a CRT routine that uses heart sounds and/or EGM signals. Furthermore, IMD 8 may deliver cardioversion or defibrillation pulses to heart 6 via any combination of electrodes 40 and housing electrode 60.

Processor 70 may detect and classify the patient's heart rhythm based on the cardiac electrical signals sensed by sensing module 76 employing any of the numerous signal-processing methodologies known in the art. In certain examples, processor 70 may provide the processed signal to cardiac signal analyzer for further processing or combination with heart sound signals. In other examples, sensing module 76 provides the cardiac electrical signals sensed directly to cardiac signal analyzer 80. In still other examples, sensing module 76 provides the senses cardiac electrical signals to both processor 70 and cardiac signal analyzer 80 for different signal processing. In various examples, processor 70 may maintain escape interval counters that may set or reset upon sensing of P-waves and R-waves by sensing module 76.

IMD 8 is configured to communicate with heart sound sensor 82, which may be remotely located relative to housing 16, e.g., as a separate component of a medical therapy system. In another example, IMD 8 may include heart sound sensor 82. In either case, heart sound sensor 82 generates an electrical signal based on senses heart sounds of patient 14, and may be implemented as a piezoelectric sensor, a microphone, an accelerometer, or other type of acoustical sensor.

In some examples, heart sound sensor 82 may be part of an integrated sensor assembly including more than one sensor. For example, an integrated sensor assembly with heart sound sensor 82 may include multiple accelerometer devices or other acoustic sensors. In examples in which the integrated sensor assembly includes one or more accelerometers, the accelerometers may be used to detect patient posture, as well as sound. An integrated sensor assembly including heart sound sensor 82 may also include one or more other sensors, such as an optical sensor, which may be used to, e.g., optically monitor blood flow or blood oxygenation through vasculature adjacent the integrated sensor assembly. Electrical sensors may be used to monitor impedance, e.g., for lung wetness and/or cardiac applications (filling waveforms etc.), and/or to monitor electrical potential, such as with ECG signals. In other examples, a sensor may not include a sound sensor, but may include one or more electrical sensing elements, one or more optical sensing elements or any combination thereof.

Any of the sensed physiological patient data may be combined or analyzed to generate a physiological metric such a cardiac metric. The physiological metric may be stored for later presentation to a clinical and/or used to evaluate the efficacy of a therapy delivered to the patient. In some examples, a generated physiological metric, such as cardiac metric, may be used to adjust therapy delivered to the patient. As one example, a combination ECG/optical/heart sound sensor would be able to monitor arrhythmias via ECG, perfusion/oxygenation via the optical sensor, and LVdPdt and other cardiac metrics via the heart sound sensor.

In the illustrated example of FIG. 3, heart sound sensor 82 is separate and remote from the IMD 8, and thus, can be implanted at target locations remote from the IMD 8, but can still wirelessly communicate with IMD 8. In other examples, heart sound sensor 82 may be formed integrally with an outer surface of housing 16. In another example, heart sound sensor 82 is located on a lead that is coupled to IMD 8. In any case, heart sound sensor 82 may wirelessly communicate with IMD 8.

Figure 4A:
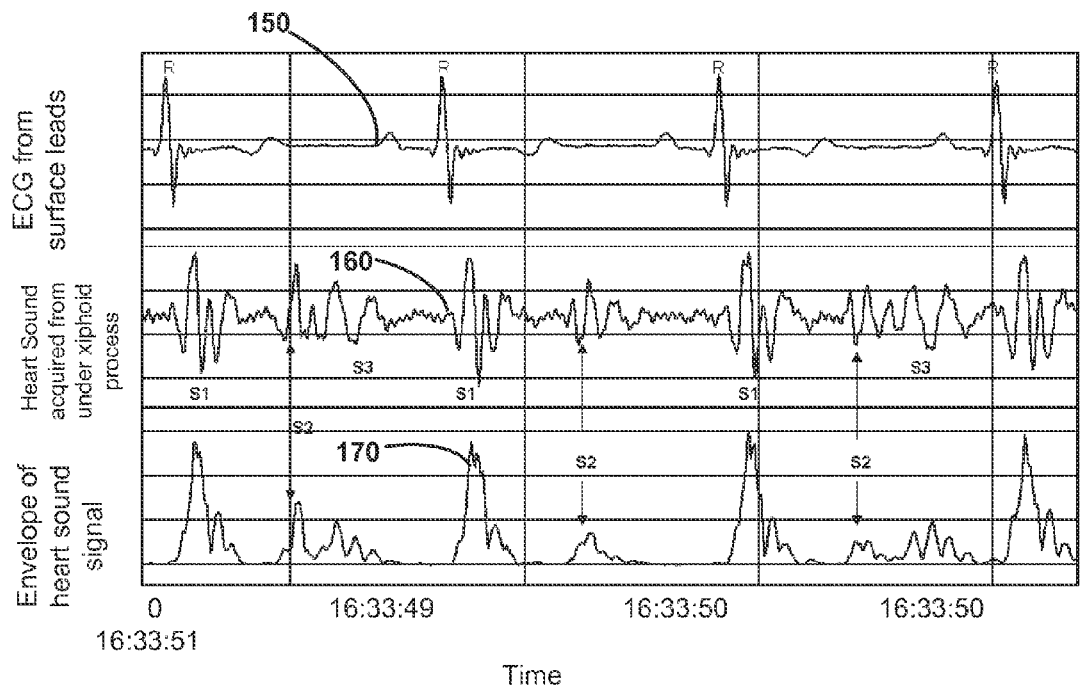
FIG. 4A illustrates example heart sound and ECG signals.

FIG. 4A illustrated three separate plots of different heart signals that may be utilized to generate one or more cardiac metrics. Specifically, plot 150 is an ECG tracing of heart signals sensed by leads mounted to the surface of a patient. Plot 150 is labeled to show the R-waves of the signal. Plot 150 also includes other cardiac metrics including the P wave, QRS complex and T wave of the electrical signal. The R-waves and other features described herein may be detected by the IMD from the cardiac EGM detected via implanted electrodes. In some examples, these features may represent cardiac metrics, or may be used as inputs to generate cardiac metrics with an IMD or other device.

Plot 160 illustrates heart sounds sensed by a sound sensor mounted under the xiphoid process of the patient, which represents one example location for mounting a sound sensor on an inner wall of the thoracic cavity of the patient. Heart sounds S1, S2 and S3 are labeled on plot 160.

Processed or filtered heart sounds, such as those represented by plots 160, 170 may be used to identify possible cardiac function, for example, the Q-S1 interval. The Q-S1 interval is a surrogate for the rate of change in pressure, LV dPdt. An increase Q-S1 interval indicates a decrease in pressure. As another example, the S1-S2 interval may be a surrogate for Left Ventricular Systolic Time (LVST); and LVST may be a surrogate for stroke volume. A decreased S1-S2 interval may represent a decreased stroke volume. In addition, the presence of either heart sound S3 or S4 may indicate left ventricle dysfunction. These features and others may be may represent cardiac metrics or may be used as inputs to generate cardiac metrics with an IMD or other device. In some examples, the monitored heart sounds may be combined with sensed cardiac EGM signals, e.g., as represented by plot 150, to generate a cardiac metric with an IMD or other device.

In addition, plot 170 represents an envelope derived from the heart sounds represented by plot 160. The S2 heart sounds are more prominent on plot 170. Features of the envelope represented by plot 170, such as the S2 heart sound, may be combined with monitored heart sounds and/or with sensed cardiac EGM or ECG signals to generate a cardiac metric with an IMD or other device.

In some examples, one or more of these cardiac metrics may be used to select from a plurality of pacing parameter settings, issue an alert, and/or determine whether to initiate CRT. In addition, cardiac metrics may be combined with other physiological metrics to select from a plurality of pacing parameter settings, issue an alert, and/or initiate CRT. In some examples, a sound sensor mounted to an inner wall of a thoracic cavity of a patient may also be used to monitor lung sounds and the lung sounds may be used to generate separate physiological metrics, or may be combined with cardiac metrics to generate a physiological metric. In one example, combining lung sounds with heart sounds might be much more specific about conditions such as heart failure status. For example, the presence of rales often indicates the buildup of fluid in the lungs, which may be another indicator of worsening heart failure status. The use of respiratory rate may also help generate a physiological metric such as an incidence of dyspnea or shortness of breath.

Figure 4B:
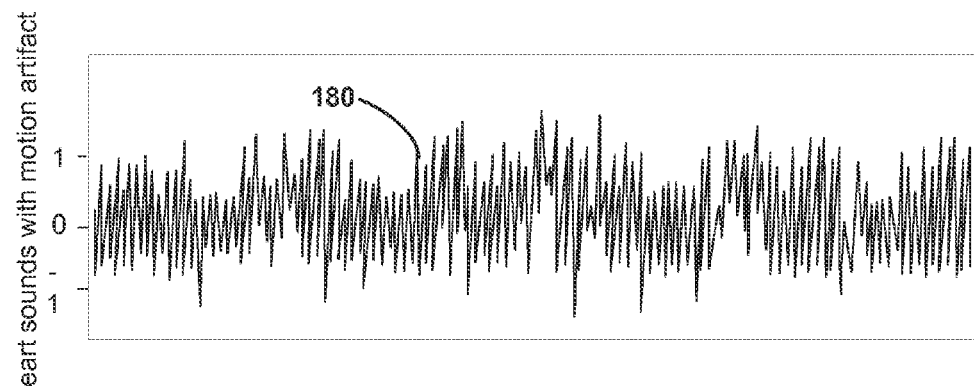
FIG. 4B illustrates an example of non-filtered signal that includes motion artifacts from a heart sounds sensor.

In contrast, FIG. 4B illustrates plot 180, which represents sounds detected by a sound sensor positioned near a skeletal muscle, e.g., such as a pectoral muscle. While positioning a sound sensor in a pectoral muscle may facilitate useful heart sound sensing while a patient is inactive, during periods of activity the sensed sound signal may be practically unusable, e.g., due to skeletal muscle motion artifacts in the signal. In this manner, plot 180 represents sounds including heart sounds as well as skeletal muscle motion artifacts. Generally, a signal including heart sounds as well as a motion artifact, like signal 180, would need to be significantly processed or filtered to obtain a useable heart sound, such as signal 170 of FIG. 4A. In some instances, it may not be possible to isolate the heart sounds of a signal including heart sounds as well as motion artifacts. In such instances, a signal like signal 180 may not include a useable heart sound.

For example, motion artifacts may occur in the same bandwidth as the heart sound signal. Motion artifacts may also have amplitudes large enough to saturate the amplifiers used for signal acquisition, rendering the output signal difficult to read or unusable. In such cases, signal-processing techniques may not be available to remove the motion artifacts, and the motion artifacts may substantially corrupt the heart sound signal. In addition, less extensive signal processing may be necessary when a signal includes fewer or less pronounced artifacts, which may reduce battery consumption and improve device longevity.

Figure 5:
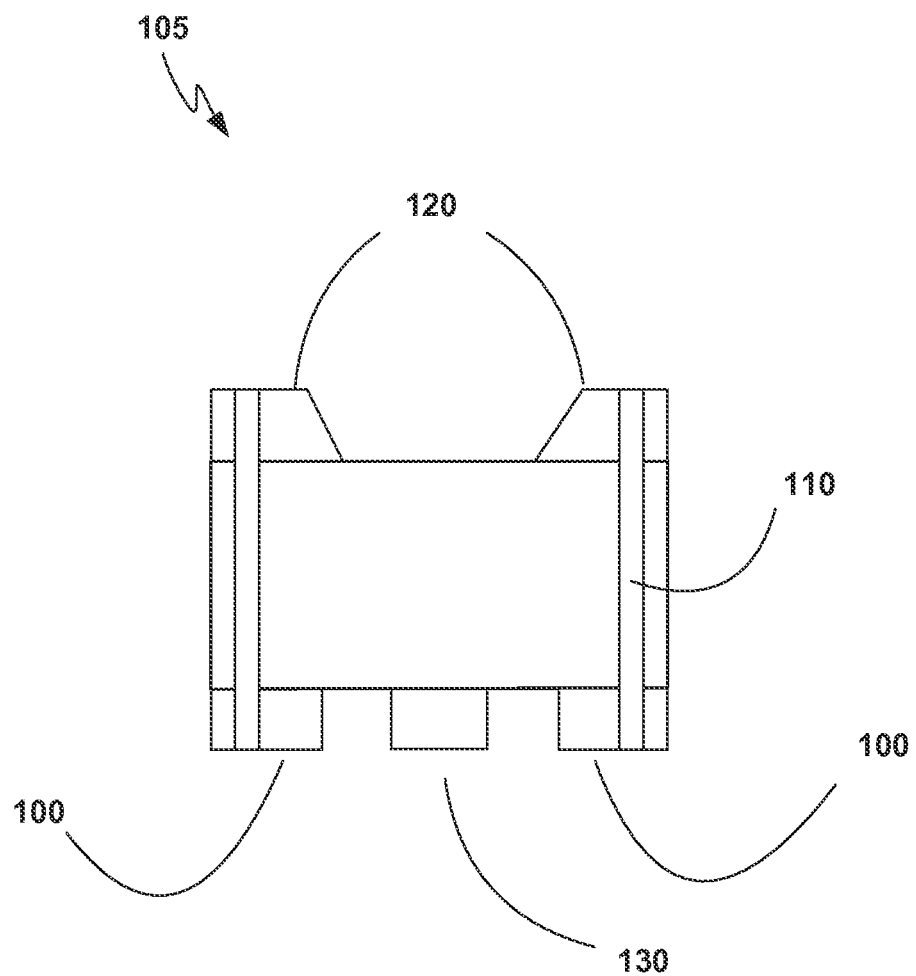
FIG. 5 is a schematic illustrating an example of an integrated sensor assembly including a sound sensor and an optical sensor, as well as ECG leads and anchors for securing the integrated sensor assembly to bone or cartilage within the thoracic cavity.

FIG. 5 is a schematic illustrating a sound sensor in an integrated sensor assembly 105. Integrated sensor assembly 105 includes a sound sensor 120 on one end that is configured to face the heart of a patient when implanted to pick up heart sounds when implanted within the thoracic cavity of the patient. In this manner, integrated sensor assembly 105 represents an example configuration of a heart sound sensor.

Integrated sensor assembly 105 may also contain ECG leads or impedance electrodes 100 that may be located on the sensor assembly side that is secured to a patient tissue, such as bone or cartilage. Electrodes 100 may be configured to monitor electrogram signals separate from those monitored by IMD 8. Electrodes 100 could, for example, pick up a P-wave of the heart.

Integrated sensor assembly 105 may also include an optical sensor 130 configured to monitor vascular activity, such as blood flow or volume. The optical sensor 130 could be located on the mounting side of the integrated sensor assembly 105 or one of the sides of the integrated sensor assembly 105 optimally positioned near the vascular source that the optical sensor 130 is monitoring. As one example, integrated sensor assembly 105 may be configured to mount to a rib of a patient and optical sensor 130 may be configured to monitor flow within a vasculature located on or in the rib of the patient.

In further examples, a sensor assembly configured to mount to an inner wall of a thoracic cavity of a patient may not include a sound sensor, but may include sensing electrodes, e.g., for cardiac potential and/or lung impedance sensing, and or optical sensors. Such sensor assemblies may be implanted within the thoracic cavity of a patient using the techniques disclosed herein with respect to sound sensors.

In the specific example, of integrated sensor assembly 105, integrated sensor assembly 105 includes anchors 110, which are configured to mount integrated sensor assembly 105 to a patient tissue such as bone, cartilage or other patient tissue. In different examples, different techniques may be used to mount a heart sound sensor, such as integrated sensor assembly 105. For example, sutures may be used as discussed with respect to FIG. 2 and sound sensor 2. As other examples, heart sound sensors may be secured to a patient tissue by, gluing or using bone morphogenic protein or cementing the sensor assembly 105 directly to bone or cartilage, using pins (or screws) going through anchor location 110 directly into bone or cartilage, or self-actuating anchors, for example nitinol) that grab the fascia or other structure beneath the sternum or completely wrap around the sternum. Suction means could also be used to secure the integrated sensor assembly 105 until the device is encapsulated or anchored. The suction of the integrated sensor assembly 105 could be accomplished, for example, by using vacuum to secure integrated sensor assembly 105 tightly to a patient tissue during implantation to facilitate permanent fixation using a different fixation technique, such as sutures, self-actuating anchors, screws, glue, and the like.

Figure 6:
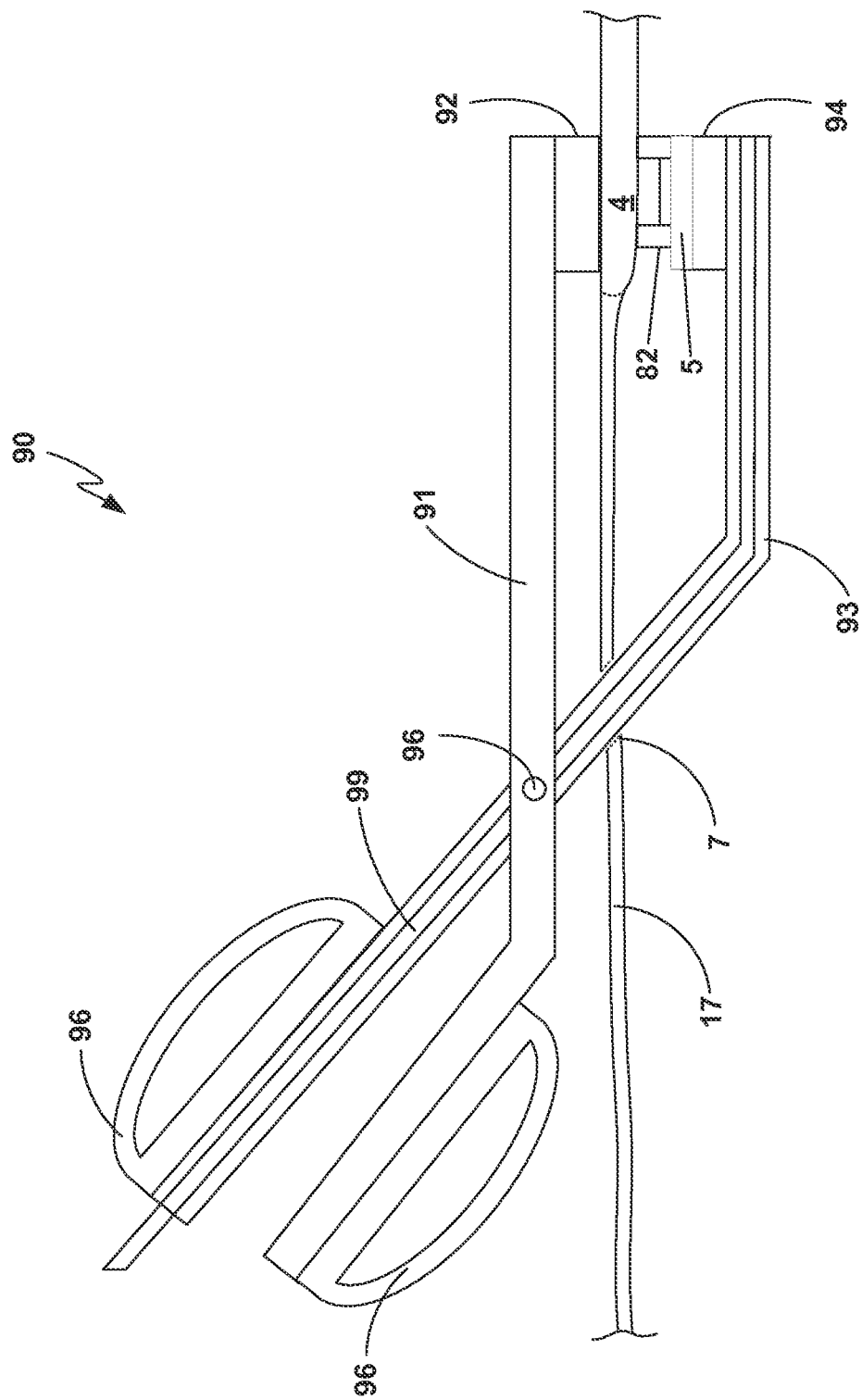
FIG. 6 is a schematic illustrating an example clamp suitable for use in the surgical implantation of a sound sensor within a thoracic cavity of a patient.

FIG. 6 is a conceptual schematic of clamping tool 90. Clamping tool 90 is an example instrument that suitable for use to implant sound sensor 82 on sternum 4 and within the thoracic cavity of a patient, such as patent 14 (FIG. 1). In some examples, sound sensor 82 may be considered substantially similar to sound sensor 2 (FIG. 2) and/or integrated sensor assembly 105 (FIG. 5).

Clamping tool 90 includes two levers 91, 93 joined at fulcrum 95. Levers 91, 93 include paddles 92, 94 at their distal ends. Handle 96 is located at the opposite ends of levers 91, 93 and may be used by a clinician to actuate clamping tool 90. Sound sensor 82 is temporarily mounted to paddle 94 to facilitate position of sound sensor 82 within the thoracic cavity of a patient and to allow sound sensor 82 to experience a clamping force applied by a clinician via handle 96. In different examples, sound sensor 82 may be temporarily mounted to paddle 94 using securing layer 5, which may include, for example, an adhesive pad, pins, a vacuum, magnet or other gripping means.

In the example of FIG. 6, sound sensor 82 is implanted on the underside of sternum 4 and within the thoracic cavity of the patient within the sub-xiphoid region. During an implantation procedure, sound sensor 82 is secured to paddle 94 such that clamping tool 90 and sound sensor 82 form an assembly. Incision 7 is made in skin 17 to access the sub-xiphoid region of the patient. As an example, incision 7 may be about one centimeter in length. The distal end of lever 93 is inserted into incision 7 such that sound sensor 82 is positioned adjacent sternum 4 within the thoracic cavity. Once the clinician determines sensor is positioned at a target implant location, the clinician operates handle 96 to compress sound sensor 82 and sternum 4 between paddles 92, 94. The pressure serves to activate fixation means on sound sensor 82 such that sound sensor 82 is secured to sternum 4. In different examples, any fixation means compatible with bone or cartilage can be utilized to anchor sound sensor 82 to sternum 4 or other patient tissue, such as gluing or using bone morphagenic protein, pins, self-actuating anchors or other techniques.

As shown in FIG. 6, sound sensor 82 is mounted to the sternum 4 on the sub-xiphoid process, but in other examples, sound sensor 82 may be mounted to a rib or other patient tissue, where the bone or cartilage material is substantially free from motion artifact, caused for example by skeletal muscle.

As shown in FIG. 6, clamping tool 90 further includes vacuum tube 99 in lever 93. In some examples, a vacuum may be applied to vacuum tube 99 during the implantation procedure. For example, accessing the thoracic cavity during the implantation of sound sensor 82 may allow air to enter the thoracic cavity via incision 7 leading to partially or fully collapsed lungs for the patient. Applying a vacuum to vacuum tube 99 during the implantation procedure may capture air entering the thoracic cavity via incision 7 to mitigate risk of collapsed lung during the procedure. In other examples, a vacuum tube separate from clamping tool 90 may be used to maintain a negative pressure within the thoracic cavity via either incision 7 or a separate incision. In a further example, lever 93 may substantially plug incision 7 during the implantation procedure such that actively maintaining a negative pressure within the thoracic cavity using a vacuum tube may not be necessary.

Figure 7:
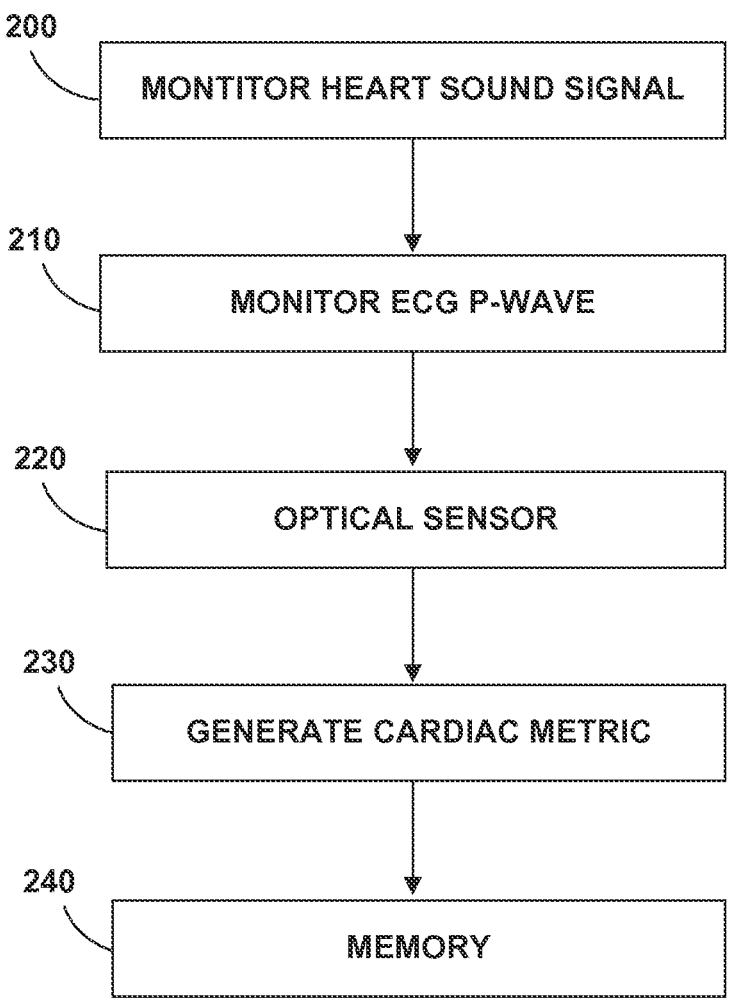
FIG. 7 is a flowchart illustrating an example method for monitoring heart sounds.

FIG. 7 is a flowchart illustrating example techniques for monitoring heart sounds. For clarity, the techniques of FIG. 7 are described with respect to the system 10 of FIG. 1. Sensor 2 is mounted within the thoracic cavity of patient 14 and monitors sounds including heart sounds from within the thoracic cavity (200). In some examples, sensor 2 may be part of an integrated sensor assembly that also monitors a cardiac signal, such as an ECG. In one example, the integrated sensor assembly monitors a P-wave of heart 6 of patient 14 from the ECG (210). In different examples, ECG leads may be part of an integrated sensor assembly include sound sensor 2 or directly or incorporated in IMD 8. In some examples, an integrated sensor assembly may include optical sensor for sensing blood flow, blood volume, and other blood related measurements (220). As one example, a combination ECG/optical/heart sound sensor would be able to monitor arrhythmias via ECG, perfusion/oxygenation via the optical sensor, and LVdPdt and other cardiac metrics via the heart sound sensor.

Signals monitored by system 10 processed by a controller that may be located in sound sensor 2, IMD 8, programmer 12 or a combination thereof to generate at least one cardiac metric based on the monitored heart sounds, and optionally any further signals monitored by system 10 (230). Because the location of the sound sensor 2 is located in the thoracic cavity where little skeletal muscle will cause motion artifact, for example on the sternum or rib 4, the need to filter the signal is substantially mitigated. The generated cardiac metric may be based on a combination of signals including audio, electrical, and/or optical signals. The cardiac metric can may be stored in a memory of sound sensor 2, IMD 8, programmer 12 or a combination thereof or transmitted from the controller to a remote device while the cardiac metric is stored in memory (240). Sound sensor 2, IMD 8, programmer 12 or any combination thereof may include all or a portion of the controller. In addition, sound sensor 2, IMD 8, programmer 12 or any combination thereof may represent a remote device that receives the cardiac metric from the controller. As these examples illustrate, the location of the controller used to generate the cardiac metric based at least in part on the monitored sounds may be located in sound sensor 2, IMD 8, programmer 12 or any combination thereof.

As previously mentioned, in some examples a cardiac signal may also be monitored with a sensor that is located either in the sound sensor 2 or in an IMD 8. The cardiac signal is traced as an electrocardiogram (ECG) and may include the P-wave of the cardiac signal 210 generate cardiac metric based at least in part on the cardiac signal. A cardiac metric can be, for example, based on any one or combination of heart sounds or electrical sensing of the cardiac signal. One example of a generated cardiac metric is where the metric is based at least in part on a heart sound, pressure within the heart, and an ECG, measuring the change in electrical potential across the cardiac tissue. In other examples, a generated cardiac metric may be based on an ECG signal, an optical signal, a heart sound signal, or any combination thereof. This information may be useful to a clinician to analyze more of the heart's 6 function rather than just one of a mechanical signal from the sound sensor 2 or the electrical signal, from the ECG, when an optical sensor is utilized, it may be positioned near an artery or other vascular member to be monitored, for example, monitoring blood flow.

In different examples, the generated cardiac metric may represent a characterization or evaluation of any number of aspects associate with the function of heart 6 of patient 14. For example, the cardiac metric may represent an indication of atrioventricular (AV) dyssynchrony based on at least an interval from heart sound S2 to heart sound S1, an indication of interventricular (VV) dyssynchrony based on a splitting of at least one of heart sound S1 and heart sound S2, an indication of left intraventricular dyssynchrony based on at least one of: electromechanical activation delay (EMAT), EMAT plus S1 duration, heart sound M1 duration, and heart sound A2 duration, a surrogate for a myocardial performance index (MPI) based at least on a duration heart sound S1 and a duration of heart sound S2, an indication of left ventricle (LV) fill time based on the interval between heart sound S2 and heart sound S1, and/or an indication of LV contractility.

Figure 8:
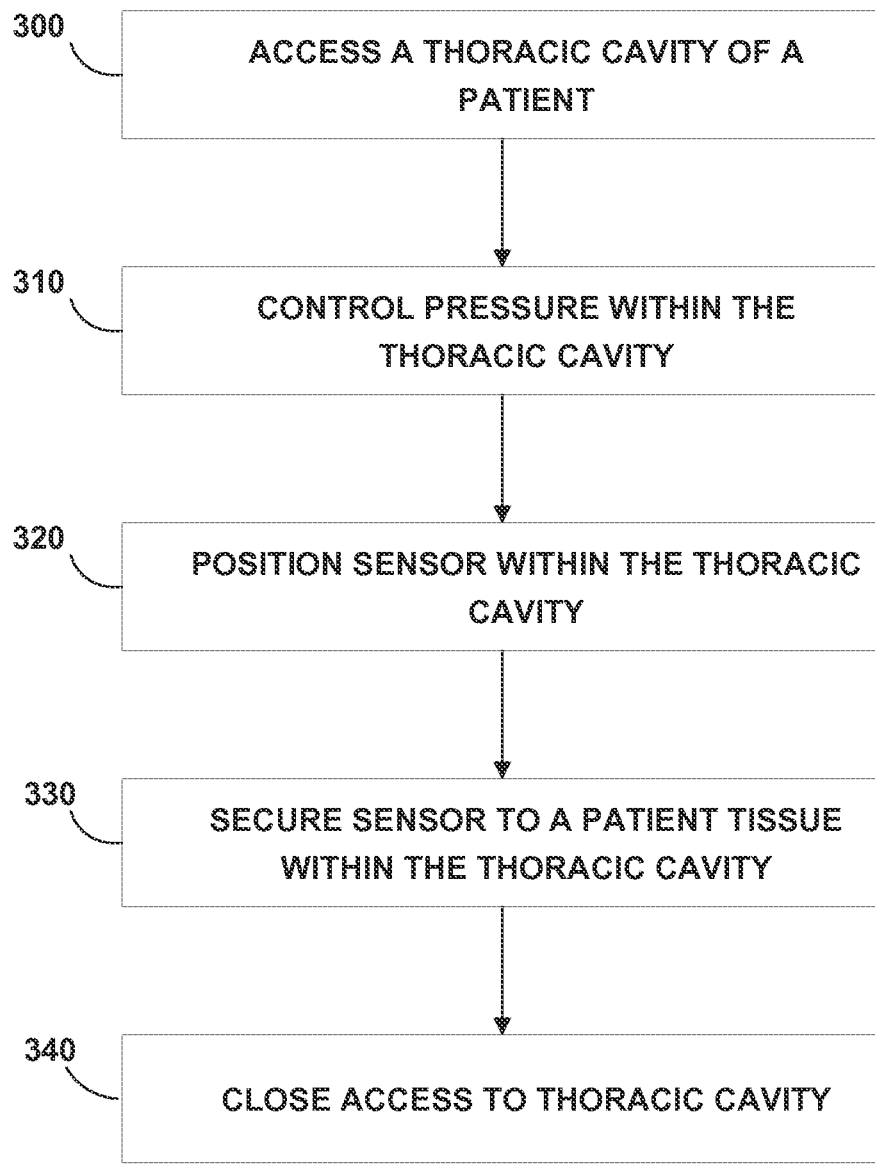
FIG. 8 is a flowchart illustrating an example method for surgically implanting a sound sensor.

FIG. 8 is a flow diagram of exemplary surgical steps for implanting a sound sensor such as sound sensor 82 (FIG. 6) within the thoracic cavity of a patient. A clinician first accesses the target implant location of the thoracic cavity of by making incision 7 (300). In some examples, incision 7 may be a puncture. Access may be accomplished by laparoscopic or by using a sharp cutting object, such as a scalpel. In some examples, incision 7 is kept to a relatively small size, such as one centimeter, so that environmental contaminants entering the incision location are greatly reduced and the surgery is less invasive, for example, the patient will not need to heal from a larger incision. When a clinician accesses the thoracic cavity, controlling air pressure may become a factor. The lungs need at least a partial vacuum as the chest muscles expand when a person inhales. If there is a leak in the walls of the thoracic cavity and a partial vacuum cannot be achieved, the lung may collapse. Thus, in some examples, air pressure may be controlled by introducing a vacuum into the thoracic cavity to mitigate a risk of lung collapse during implantation of the sound sensor (310). In other examples, a patient may be connected to a ventilator during an implantation procedure such that the lungs are actively expanded even if there is a leak in the walls of the thoracic cavity.

The clinician introduces sound sensor 82 into the thoracic cavity of the patient positioning the sound sensor proximate to the target implant location within the thoracic cavity via the access space (320). Many possible tools for placing the sound sensor 82 into the thoracic cavity may be used. One example is the use of surgical clamp 90. Lever 93 of clamp 90 optionally includes vacuum tube 99 to control pressure within the thoracic cavity of the patient during the implantation.

Actuating handles 96 (FIG. 6) allow a clinician to grip the sound sensor 82 and allow the clinician to place the sound sensor 82 in a target implant location on a patient tissue within the thoracic cavity, for example, on the sternum, rib, or xiphoid process. In some examples, the clinician may use fluoroscopy or other imaging techniques to assist in locating sound sensor 82 at the target implant location. Clamp 90 allows the clinician to grip the patient tissue and securely place the sound sensor on the patient tissue so that the sound sensor 82 may be secured to the patient tissue by, for example, using a suture, a cement, a glue, an anchor, or pins (330).

Once the sound sensor is secured to a patient tissue within the thoracic cavity, the clinician may check the sound sensor to verify proper function and operation with an implantable medical device, e.g., by communicating with sound sensor via telemetry using a remote device, such as programmer 12 (FIG. 1). Clamp 90 is retracted and the clinician closes the access to the thoracic cavity, e.g., by suturing incision 7 (340).

Various examples have been described. These and other examples are within the scope of the following claims.

What is claimed is:

1. A method comprising:
accessing a thoracic cavity of a patient;
controlling air pressure within the thoracic cavity of the patient via a vacuum to mitigate a risk of lung collapse during implantation of a sensor, wherein the sensor comprises a sound sensor;
positioning the sensor within the thoracic cavity of the patient;
securing the sensor to an inner wall of the thoracic cavity;
monitoring a physiological characteristic of a patient with the sensor secured to the inner wall of the thoracic cavity of the patient; and
sending a signal based on the monitored physiological characteristic from the sensor to a remote device.

2. The method of claim 1, wherein the remote device is an implantable medical device implanted within the patient.

3. The method of claim 1, wherein securing the sensor to the inner wall of the thoracic cavity includes securing the sensor beneath the xyphoid process of the patient.

4. The method of claim 1, wherein the sound sensor includes a sound sensing element, the method further comprising monitoring heart sounds of the patient with the sound sensing element.

5. The method of claim 1, wherein the sensor includes an electrical sensing element, the method further comprising sensing an ECG of the heart of the patient with the electrical sensing element.

6. The method of claim 1, wherein the sensor includes an electrical sensing element, the method further comprising sensing an impedance of at least one of tissue or fluid of the patient with the electrical sensing element.

7. The method of claim 1, wherein the sensor includes an electrical sensing element, the method further comprising sensing an impedance of at least one of a cardiac tissue or blood of the patient with the electrical sensing element.

8. The method of claim 1, wherein the sensor includes an optical sensing element, the method further comprising monitoring blood flow in a vasculature of the patient with the optical sensing element.

9. The method of claim 1, wherein the sensor includes an optical sensing element, the method further comprising monitoring blood oxygenation in a vasculature of the patient with the optical sensing element.

10. The method of claim 1, wherein the sensor includes two or more sensing elements selected from a group consisting of:
an accelerometer;
an optical sensing element
an electrical sensing element; and
a sound sensing element.

11. The method of claim 1, wherein securing the sound sensor to the inner wall of the thoracic cavity comprises securing the sound sensor using at least one of a group consisting of:
- a suture;
- a cement;
- a glue; and
- vacuum.

12. The method of claim 1, wherein securing the sensor to the inner wall of the thoracic cavity comprises clamping the sensor to the inner wall of the thoracic cavity using a clamping tool by compressing the sensor and patient tissue forming the inner wall of the thoracic cavity between two levers of the clamping tool.

13. The method of claim 1,
wherein accessing the thoracic cavity of the patient includes cutting tissue of the patient to form an incision adjacent to a target implant location for the sound sensor, the method further comprising:
inserting a surgical tool into the incision to spread the cut tissue to provide access to the target implant location by creating an access space sufficiently wide to receive the sensor;
positioning the sensor proximate to the target implant location within the thoracic cavity via the access space;
securing the sensor to the target implant location within the thoracic cavity, wherein the target implant location is proximate at least one of a sternum, a rib cage, or a xiphoid process of the patient by at least one of a clamp, a cement, a glue, or a suture;
checking the sensor to verify proper function and operation with an implantable medical device once it is secured to the inner wall of the thoracic cavity;
retracting the surgical tool from the spread cut; and
suturing the cut tissue closed at the incision location.

14. The method of claim 13, wherein the surgical tool comprises a clamping tool comprising:
a first lever with; and
a second lever pivotally mounted to the first lever,
wherein securing the sensor to the inner wall of the thoracic cavity comprises clamping the sensor to the inner wall of the thoracic cavity using the clamping tool by compressing the sensor and patient tissue forming the inner wall of the thoracic cavity between the first and second levers of the clamping tool such that a distal end of the first lever presses on an exterior side of the patient while a distal end of the second lever presses on the sensor within the thoracic cavity.

15. A method comprising:
accessing a thoracic cavity of a patient;
controlling air pressure within the thoracic cavity of the patient via a vacuum to mitigate a risk of lung collapse during implantation of a sound sensor;
positioning the sound sensor within the thoracic cavity of the patient;
securing the sound sensor to an inner wall of the thoracic cavity;
monitoring sounds with the sound sensor secured to the inner wall of the thoracic cavity of the patient; and
sending a sound signal based on the monitored sounds from the sound sensor to a controller of an implantable medical device implanted within the patient.

16. The method of claim 15, wherein the monitored sounds include monitored heart sounds, the method further comprising generating at least one cardiac metric based on the monitored heart sounds.

17. The method of claim 15, further comprising:
monitoring posture of the patient with a posture sensor; and
generating at least one cardiac metric by analyzing the sound signal in combination with the monitored posture.

18. The method of claim 15, further comprising:
sensing a cardiac electrogram signal with the implantable medical device; and
analyzing the sound signal in combination with the cardiac electrogram signal to generate the at least one cardiac metric.

19. The method of claim 18, wherein sensing the sound signal with the implantable medical device and analyzing the sound signal in combination with the cardiac electrogram signal to generate the at least one cardiac metric includes generating one or more acoustic cardiographic metrics based on the heart sounds and the cardiac electrogram signal.

20. The method of claim 15, wherein the sound sensor is included in an integrated sensor assembly, wherein the integrated sensor assembly further includes at least one of a group consisting of:
- an accelerometer;
- an ECG sensor;
- an optical sensor;
- a posture sensor; and
- an impedance sensor.

21. The method of claim 15, wherein the sound sensor is implanted on a patient tissue selected from a group consisting of:
- a sternum of the patient;
- a rib cage of the patient; and
- a xiphoid process of the patient.

22. The method of claim 15, wherein the monitored sounds include monitored lung sounds, the method further comprising generating a respiration metric based on the monitored lung sounds.

23. The method of claim 15, wherein securing the sound sensor to the inner wall of the thoracic cavity comprises clamping the sound sensor to the inner wall of the thoracic cavity using a clamping tool by compressing the sound sensor and patient tissue forming the inner wall of the thoracic cavity between two levers of the clamping tool.

* * * * *